(12) United States Patent
Bai et al.

(10) Patent No.: US 11,061,151 B2
(45) Date of Patent: Jul. 13, 2021

(54) HYBRID TOF AND NON-TOF PET SYSTEMS WITH JOINT TOF AND NON-TOF IMAGE RECONSTRUCTION

(71) Applicant: KONINKLIJKE PHILIPS N.V., Eindhoven (NL)

(72) Inventors: Chuanyong Bai, Solon, OH (US); Andriy Andreyev, Willoughby Hills, OH (US); Bin Zhang, Cleveland, OH (US); Zhiqiang Hu, Twinsburg, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 113 days.

(21) Appl. No.: 16/466,587

(22) PCT Filed: Dec. 4, 2017

(86) PCT No.: PCT/EP2017/081280
§ 371 (c)(1),
(2) Date: Jun. 4, 2019

(87) PCT Pub. No.: WO2018/104188
PCT Pub. Date: Jun. 14, 2018

(65) Prior Publication Data
US 2019/0346577 A1 Nov. 14, 2019

Related U.S. Application Data

(60) Provisional application No. 62/430,415, filed on Dec. 6, 2016.

(51) Int. Cl.
| G01T 1/29 | (2006.01) |
| A61B 6/03 | (2006.01) |
| A61B 6/00 | (2006.01) |

(52) U.S. Cl.
CPC ............ *G01T 1/2985* (2013.01); *A61B 6/037* (2013.01); *A61B 6/4208* (2013.01)

(58) Field of Classification Search
CPC ...... G01T 1/2985; A61B 6/037; A61B 6/4208
See application file for complete search history.

(56) References Cited

U.S. PATENT DOCUMENTS

| 2003/0193029 | A1* | 10/2003 | Shao | ...................... | G01T 1/1644 |
| | | | | | 250/363.03 |
| 2009/0324042 | A1* | 12/2009 | Laurence | .............. | G01T 1/2985 |
| | | | | | 382/131 |

(Continued)

OTHER PUBLICATIONS

Eriksson, L. et al "LuYAP/LSO Phoswich Detectors for High Resolution Positron emission Tomography", Nuclear Science Symposium Conf. Record Oct. 30, 2010, pp. 3122-3125.

(Continued)

*Primary Examiner* — David P Porta
*Assistant Examiner* — Djura Malevic (57) ABSTRACT

A positron emission tomography (PET) detector array includes an enclosing radiation detector array (10) comprising radiation detector elements (14, 16) effective for detecting 511 keV radiation emanating from inside the radiation detector array. The radiation detector pixels of the cylindrical radiation detector array include both higher speed radiation detector elements (14) and lower speed radiation detector elements (16). The lower speed radiation detector pixels have a temporal resolution that is coarser than a temporal resolution of the higher speed radiation detector pixels.

18 Claims, 8 Drawing Sheets

(56) References Cited

U.S. PATENT DOCUMENTS

| | | | |
|---|---|---|---|
| 2010/0098312 A1* | 4/2010 | Leahy | G01T 1/2985 |
| | | | 382/131 |
| 2010/0108896 A1* | 5/2010 | Surti | G01T 1/00 |
| | | | 250/363.04 |
| 2012/0070050 A1* | 3/2012 | Panin | G06T 11/005 |
| | | | 382/131 |
| 2012/0070057 A1* | 3/2012 | Zhang | G06T 11/005 |
| | | | 382/131 |
| 2015/0065854 A1* | 3/2015 | Ahn | A61B 6/037 |
| | | | 600/411 |

OTHER PUBLICATIONS

International Search Report and Written Opinion for PCT/EP2017/081280.

* cited by examiner

HYBRID TOF AND NON-TOF PET SYSTEMS WITH JOINT TOF AND NON-TOF IMAGE RECONSTRUCTION

CROSS-REFERENCE TO PRIOR APPLICATIONS

This application is the U.S. National Phase application under 35 U.S.C. § 371 of International Application No. PCT/EP2017/081280, filed on Dec. 4, 2017, which claims the benefit of U.S. Provisional Patent Application No. 62/430,415, filed on Dec. 6, 2016. These applications are hereby incorporated by reference herein.

FIELD

The following relates generally to the medical imaging arts, nuclear imaging arts, positron emission tomography arts, and related arts.

BACKGROUND

Time-of-flight (TOF) positron emission tomography (PET) imaging provides TOF localization of a positron-electron annihilation event along the line of response (LOR) defined by the emitted oppositely directed 511 keV gamma rays, based on the time difference (or lack thereof) between the detections of the two gamma rays. TOF-PET has shown superior performance as compared to non-TOF PET in lesion detection, data inconsistence handling, and iterative image reconstruction convergence. The associated cost, however, can be high. The TOF associated cost includes the higher cost of crystals with the requisite speed, high-speed time stamping electronics, and operating costs such as extra TOF calibration, etc.

Accordingly, hospitals and other medical institutions make a performance-versus-cost decision as to whether to purchase and operate a TOF-PET with its superior performance, or a standard PET at lower cost but with sacrifice of some performance. Other trade-offs may be made, such as purchasing a TOF-PET scanner, but one with a reduced field of view (FOV) in the axial and/or radial direction(s) to reduce cost. This provides the superior TOF-PET performance, but at the cost of requiring longer scan times or acquiring images with undesirably truncated FOV. In the case of reduced radius detector rings, a reduction in maximum patient girth may be imposed as well.

Improvements disclosed herein address the foregoing and other disadvantages of existing radiology reading systems, methods, and the like.

BRIEF SUMMARY

In accordance with one illustrative example, a positron emission tomography (PET) detector array includes an enclosing radiation detector array comprising radiation detector elements effective for detecting 511 keV radiation emanating from inside the radiation detector array. The radiation detector pixels of the radiation detector array include both higher speed radiation detector pixels and lower speed radiation detector pixels. The lower speed radiation detector pixels have a temporal resolution that is coarser than a temporal resolution of the higher speed radiation detector pixels.

In accordance with another illustrative example, a positron emission tomography (PET) imaging device includes a radiation detector array comprising both time-of-flight (TOF) radiation detector pixels and lower speed radiation detector pixels. The lower speed radiation detector pixels have a temporal resolution that is coarser than a temporal resolution of the TOF radiation detector pixels. The imaging device also includes an electronic processor, and a non-transitory storage medium storing instructions readable and executable by the electronic processor to perform operations including: generating TOF lines of response (LORs) with TOF localization from coincident 511 keV detection event pairs both detected by TOF radiation detector pixels of the radiation detector array; generating coarse LORs from coincident 511 keV detection event pairs in which at least one event of the pair is detected by a lower speed radiation detector pixel of the radiation detector array, the coarse LORs being generated with no TOF localization or with TOF localization that is coarser than the TOF localization of the TOF LORs; and reconstructing a PET data set comprising both the TOF LORs and the coarse LORs to generate a reconstructed image.

In accordance with another illustrative example, a non-transitory storage medium store instructions readable and executable by at least one processor to perform a positron emission tomography (PET) image reconstruction method. The method includes: receiving or generating a PET data set comprising counts along lines of response (LORs) wherein the PET data set includes at least first count type with time-of-flight (TOF) localization and second count type with no TOF localization or with TOF localization that is coarser than the TOF localization of the first LORs; and reconstructing the entire PET data set including both the first count type and the second count type to generate a reconstructed image.

One advantage resides in providing PET imaging with improved lesion detection, data inconsistence handling, reconstruction convergence and/or other benefits associated with TOF-PET but with reduced cost compared with existing TOF-PET devices.

Another advantage resides in providing TOF-PET imaging with reduced cost.

Another advantage resides in providing TOF-PET detector arrays that include lower-cost detector pixels in peripheral portions of the array where TOF performance improvement is of reduced benefit.

Another advantage resides in providing a TOF-PET device that provides a tailored trade-off between TOF performance enhancement and device cost.

Another advantage resides in providing a TOF-PET device with axially extended field of view at reduced cost.

Further advantages of the present disclosure will be appreciated to those of ordinary skill in the art upon reading and understand the following detailed description. It will be appreciated that a given embodiment may provide none, one, two, or more of these advantages.

BRIEF DESCRIPTION OF THE DRAWINGS

The present disclosure may take form in various components and arrangements of components, and in various steps and arrangements of steps. The drawings are only for purposes of illustrating the preferred embodiments and are not to be construed as limiting the disclosure.

DETAILED DESCRIPTION

It is recognized herein that there are various situations in which one may consider using non-TOF or low-resolution TOF detectors together with high-resolution TOF detectors to reduce the cost while still taking advantage of TOF imaging. Some examples are presented below.

Example 1. Detector sensitivity at the end of the axial field-of-view (FOV) of a PET system is very low as compared to the center of the axial FOV due to the geometric response of the detector. This implies that high performing TOF detectors at the end of the axial FOV are not fully utilized. In some embodiments disclosed herein, such TOF detectors are replaced with non-TOF detectors or TOF detectors with lower temporal resolution in order to reduce the cost. In a variant embodiment, non-TOF or lower-resolution TOF detectors are added to the end of the axial FOV so as to enlarge the axial FOV without the full cost of adding additional peripheral high speed TOF detector rings.

Example 2. For multiple ring PET detectors, interleaved TOF and non-TOF detector rings, or interleaved high-resolution TOF and lower-resolution TOF rings, may be used for cost reduction. By selecting the ratio of TOF versus non-TOF (or lower resolution TOF) detector rings, a performance versus cost trade-off can be tailored.

Example 3. For detector arrays constructed as modules, e.g. each detector module including an N×M (sub-)array of detector pixels, one may mix TOF and non-TOF detector modules in predefined patterns to achieve cost reduction and sufficient TOF imaging benefit. Again, this permits tailoring of a performance versus cost trade-off.

Time-of-flight (TOF) localization significantly improves image quality, (e.g. resolution and practical performance for reconstruction convergence and lesion detection). However, TOF components are generally more expensive than non-TOF components. For example, TOF detectors require faster scintillator crystals, faster detectors, and more complex signal processing and time stamping circuitry.

Disclosed herein are embodiments in which a (usually multi-ring) PET detector array includes a mix of TOF detectors and non-TOF detectors. In variant embodiments, the mix is of higher speed TOF detectors and lower speed TOF detectors (lower speed, but still fast enough to provide useful TOF localization). To be beneficial, the added non-TOF detectors should add performance versus using the TOF detectors alone (otherwise improved performance and lower cost could be achieved by providing only the TOF detectors as is conventionally done in TOF-PET). Data processing aspects disclosed herein enable the use of a mix of TOF and non-TOF detectors to produce superior imaging versus the TOF detectors alone.

In one illustrative embodiment, a multi-ring PET detector array includes central detector rings which include exclusively TOF detectors, and (axially) outer detector rings that are exclusively non-TOF (or slower TOF) detectors. By segregating the different detector types on different PET detector rings, manufacturing is simplified. Placing the slower detectors on the peripheral rings provides highest TOF benefit for the central portion of the FOV, where the organ or other region of greatest interest is usually located in the field of view (FOV).

In another illustrative embodiment, the TOF detectors and the non-TOF or slower TOF detectors are interleaved at the individual detector level or at some higher level (e.g. at the module level in detector arrays constructed of N×M modules). This approach can provide improved uniformity, at the cost of possibly greater manufacturing complexity.

In the disclosed mixed TOF/non-TOF PET detector array, a given line of response (LOR) can be one of three types, each having different temporal resolution. The fastest LOR type has TOF detectors providing the detection of both oppositely directed 511 keV gamma rays produced by an electron-positron annihilation event. These fast LORs have the best temporal resolution for the TOF information. The slowest (non-TOF) LOR type is the one connecting a pair of non-TOF detectors (or a pair of non-TOF and TOF detectors) detecting both 511 keV gamma rays, and has the poorest or non-existent temporal resolution. LORs of the intermediate type have one gamma ray detected by a TOF detector and the other by slower TOF detector, and thus have intermediate temporal resolution.

Various reconstruction approaches may be used to leverage the TOF and non-TOF detectors. In a cyclical approach, TOF data are reconstructed using TOF reconstruction, the resulting image is fed into a non-TOF reconstruction of the non-TOF data (e.g. as a prior image to penalize large deviations from the TOF image, or as a initial image estimate), and the resulting non-TOF image is fed back to a successive iteration of the TOF reconstruction, and so forth. In another reconstruction approach, the back projection formula is employed, with projection and back projection operators $H_{ij}$ and $H_{ji}$ characterizing the contribution of counts j to image content at image voxel i. In this approach, a TOF kernel is employed whose width is appropriate for temporal resolution of the given count j. If the timing resolution for the one of the detector element that form the count j along LOR is denoted $\sigma_F$ and the timing resolution for the other endpoint is denoted $\sigma_S$, then $\sigma_j=\sqrt{(\sigma_F)^2+(\sigma_S)^2}$ is the width for the resulting timing resolution of the count j.

Figure 1:
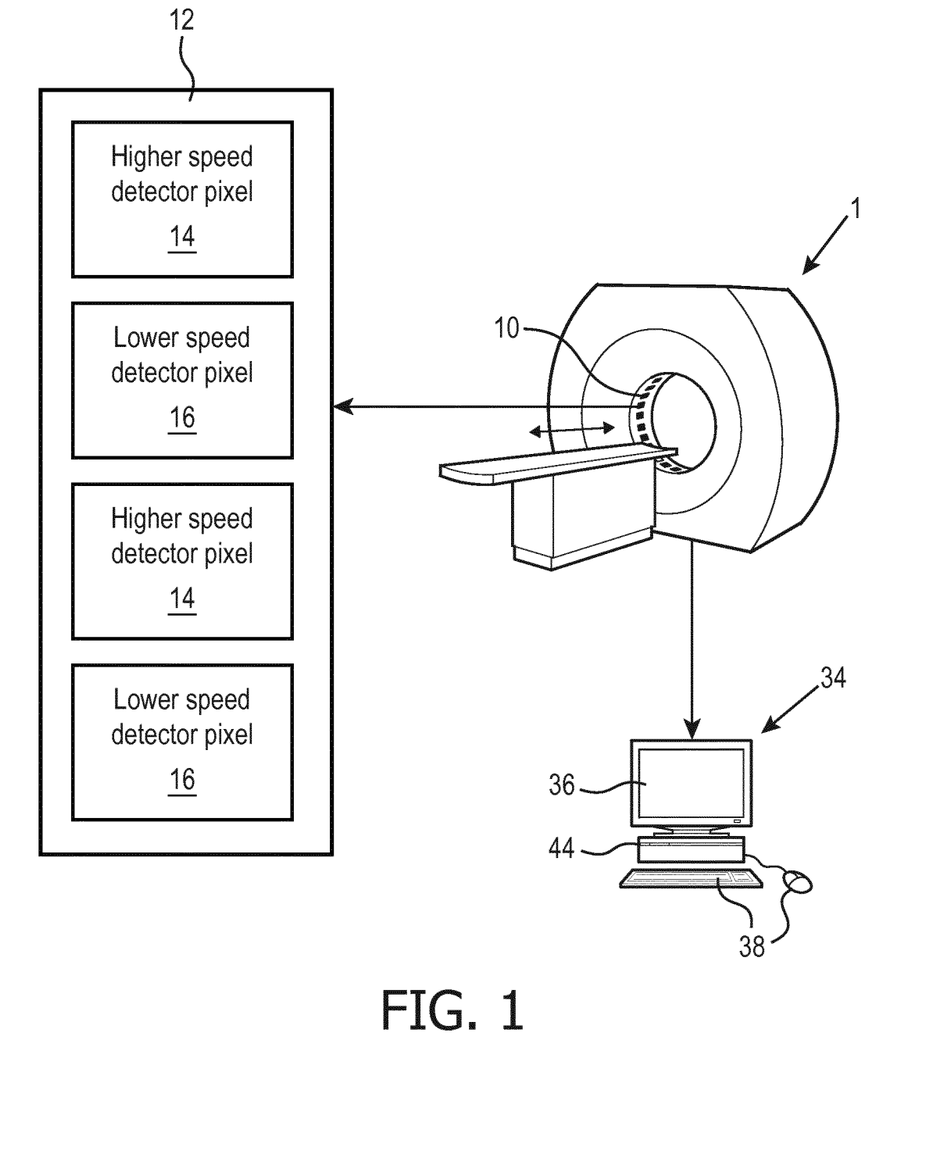
FIG. 1 diagrammatically illustrates a PET imaging device.

With reference now to FIG. 1, a schematic illustration of a PET detector array 10 for a PET imaging device 1 is shown. By way of some non-limiting illustrative examples, the illustrative PET imaging device 1 may be the PET gantry of a Vereos™ Digital PET/CT scanner or an Ingenuity™ TF PET scanner, (both available from Koninklijke Philips N.V., Eindhoven, the Netherlands, modified as disclosed herein). The illustrative PET detector array 10 is an array that encloses one or more detectors, such as a cylindrical radiation detector array, and comprises detector pixels indicated in a diagrammatic detector array layout 12. The cylindrical radiation detector array 10 includes radiation detector elements 14, 16 (e.g., pixels, tiles, modules, rings, and the like) that are effective for detecting 511 keV radiation emanating from inside the cylindrical radiation detector array 10. The radiation detector pixels include higher speed radiation detector pixels 14 and lower speed radiation detector pixels 16. The lower speed radiation detectors pixels 16 have a temporal resolution $\sigma_S$ that is coarser than a temporal resolution $\sigma_F$ of the higher speed radiation detector pixels 14 (e.g., $\sigma_S > \sigma_F$).

The higher speed radiation detector pixels 14 may, by way of non-limiting illustrative embodiment, include one of Lutetium oxyorthosilicate (LSO), Lutetium-yttrium oxyorthosilicate (LYSO), Lutetium Fine Silicate (LFS) or Lanthanum Bromide (LaBr) or the like, scintillators, and the lower speed radiation detector pixels 16 may, by way of non-limiting illustrative embodiment, include Bismuth Germanate Oxide (BGO) or Sodium Iodide (NaI) or the like, scintillators. Light detector elements such as photomultiplier tubes (PMTs) or solid-state silicon photomultiplier (SiPM) devices are arranged to detect scintillation light generated in the scintillators. The timing resolution provided by the given PMT or SiPM device (depending on the build quality and related cost) may vary even for the same crystal type. In some embodiments, there is a one-to-one association between scintillator crystals and the light detector elements, with each scintillator/light detector element forming a single radiation detector pixel. In other embodiments, such a one-to-one correspondence may not be present when using PMT-based readout, and individual radiation detector pixels are defined in the readout circuitry, e.g. using Anger logic. It is also contemplated in alternative embodiments for the radiation detector pixels to be direct radiation detectors, e.g. Cadmium Zinc Telluride (CZT)-based semiconductor detector elements that directly absorb and detect 511 keV photons.

Figure 2:
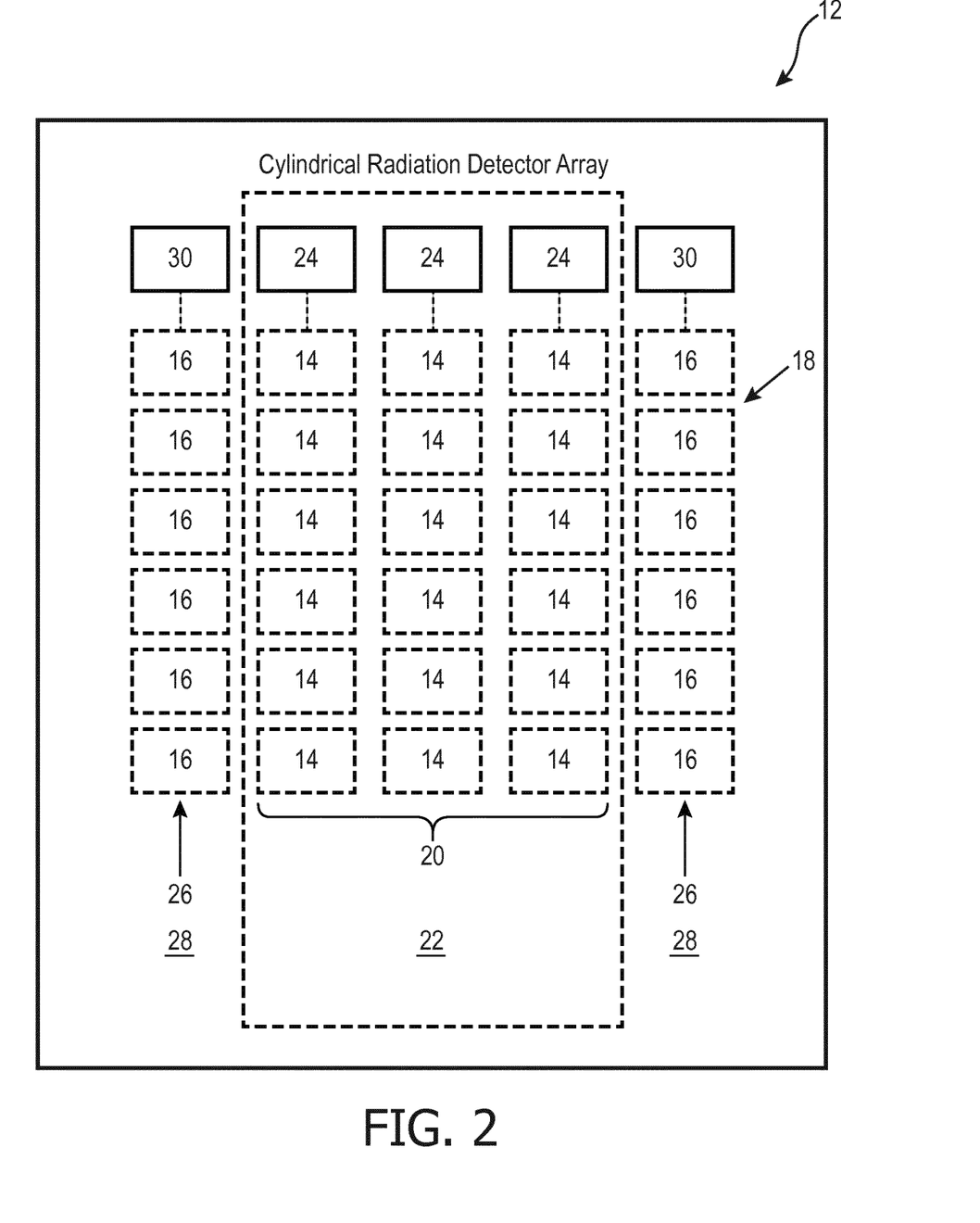
FIG. 2 diagrammatically illustrates an embodiment of a PET detector array of the PET imaging device of FIG. 1.

In one embodiment, as shown in FIG. 2, the cylindrical radiation detector array 10 has a detector array layout 12 that includes a plurality of radiation detector rings 18 arranged to form the cylindrical radiation detector array. The radiation detector rings 18 include central radiation detector rings 20 that form a central portion 22 of the cylindrical detector array. Each central radiation detector ring 20 exclusively includes the higher speed radiation detector pixels 14. In other words, each central radiation detector ring 20 does not include any of the lower speed radiation detector pixels 16. Each central radiation detector ring 20 includes TOF timestamp circuitry 24 configured to generate or assign time stamps for 511 keV radiation detection events detected by the higher speed radiation detector pixels 14 with temporal resolution effective to provide TOF localization along lines of response (LORs).

The radiation detector rings 18 also include peripheral radiation detector rings 26 that form peripheral portions 28 of the cylindrical detector array 12. The peripheral radiation detector rings 26 surround the central radiation detector rings 20. Each peripheral radiation detector ring 26 exclusively includes the lower speed radiation detector pixels 16. In other words, each peripheral radiation detector ring 26 does not include any of the higher speed radiation detector pixels. Each peripheral radiation detector ring 26 includes non-TOF timestamp circuitry 30 configured to generate time stamps for 511 keV radiation detection events detected by the lower speed radiation detector pixels 16 with temporal resolution that is too coarse to provide TOF localization along LORs. In a variant embodiment, the lower speed radiation detector pixels provide sufficient speed for TOF localization, but with lower temporal resolution than is provided by the (higher speed) TOF detectors 14. In this case the timestamp circuitry 30 may again be lower speed than the timestamp circuitry 24.

Figure 3:
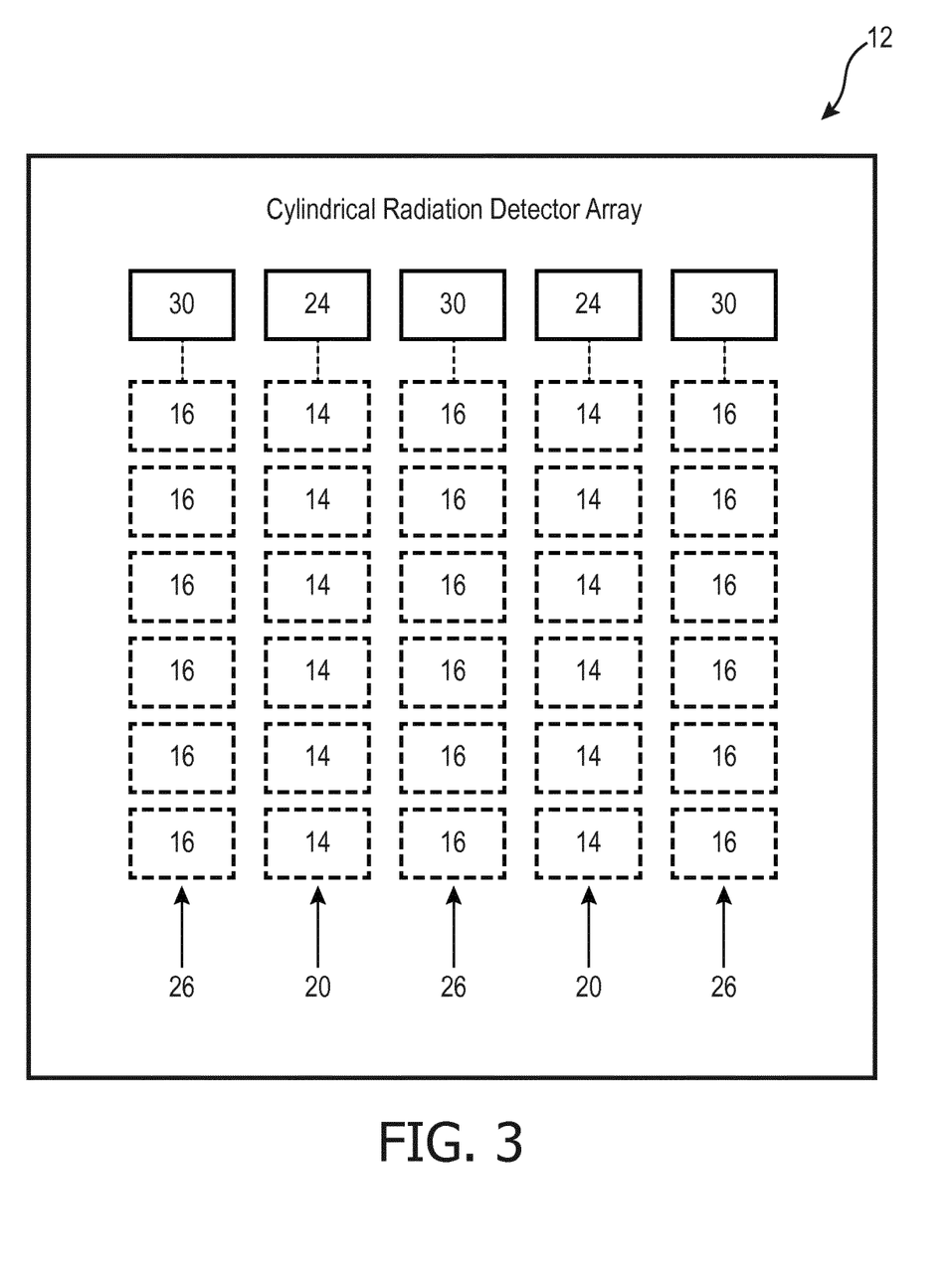
FIG. 3 diagrammatically illustrates an embodiment of a PET detector array of the PET imaging device of FIG. 1.

In another embodiment, as shown in FIG. 3, the cylindrical radiation detector array 10 has a detector array layout 12 that interleaves the TOF detector rings 20 comprising exclusively TOF detector pixels 14 and the non-TOF detector rings 26 comprising exclusively non-TOF detector pixels 16. Each detector ring 20 again includes the corresponding TOF timestamp circuitry 24, and each detector ring 26 again includes the corresponding non-TOF timestamp circuitry 30. As with the embodiment of FIG. 2, in a variant of the embodiment of FIG. 3 the detector pixels 16 may alternatively be slower-speed TOF detector pixels (as compared with the detector pixels 14). In this embodiment, each LOR can be detected by the lower speed radiation detector pixels 16. The lower speed radiation detector pixels 16 can be connected to the TOF timestamp circuitry 24 so that the TOF timestamp circuitry can process the LORs detected by the lower speed radiation detector pixels to provide coarse TOF localization along the LORs.

Although not illustrated, it is also contemplated to mix TOF detector pixels 14 and non-TOF detector pixels 16 within a single detector ring. For example, if each detector ring is constructed of a set of rectangular detector modules each containing a (sub-)array of N×M detector pixels, then some such detector modules may include TOF detectors 14 and associated timestamp circuitry 24 while other detector modules on the same detector ring may include non-TOF detectors 16 and associated timestamp circuitry 30.

Referring back to FIG. 1, the PET imaging device 1 also includes at least one computer or other electronic data processing device 34 for performing image reconstruction operations. The illustrative at least one computer 34 includes typical components, such as at least one display component 36, and at least one user input component 38. The computer 12 includes least one electronic processor 44 (e.g. a microprocessor, multi-core microprocessor, or so forth) programmed to perform calibration functions as disclosed herein. In some examples, the display 36 can be a touch-sensitive display. The user input component 38 can be a mouse, a keyboard, a stylus, an aforementioned touch-sensitive display, a microphone, and/or the like.

Figure 4:
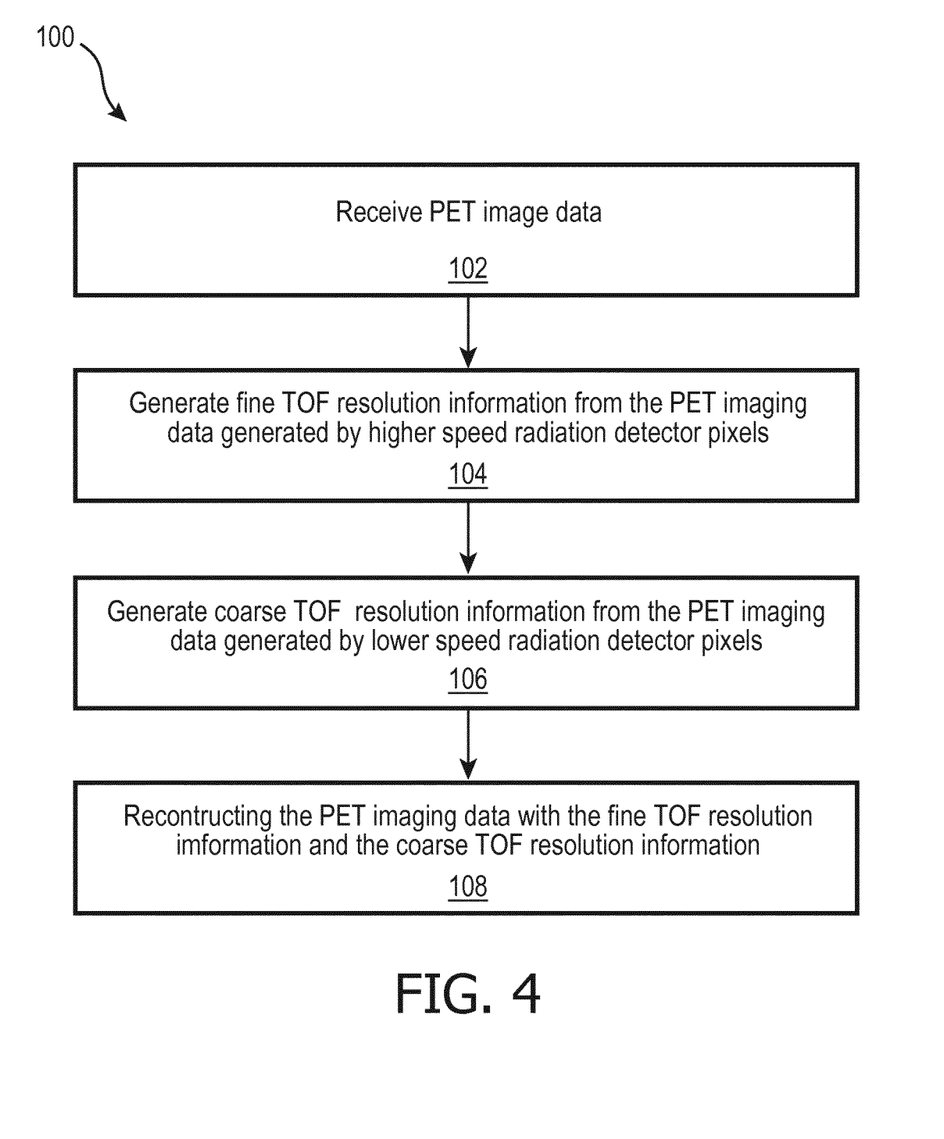
FIG. 4 is an exemplary flow chart of an image reconstruction process of the apparatus of FIG. 1.

With reference now to FIG. 4, the at least one processor 44 is programmed to perform a PET image reconstruction method 100 with operations 102-108. At 102, PET imaging data is received at the computer 34 from the PET imaging device 1. At 104, fine resolution information is generated from the imaging data generated by the higher speed radiation detector pixels 14. At 106, coarse resolution information is generated from the imaging data generated by the lower speed radiation detector pixels 16. At 108, the PET imaging data is reconstructed from counts possessing both the fine resolution information and the coarse resolution information.

In one embodiment, 102 can include receiving a PET imaging data set directly from the PET imaging device 1. For example, the PET data imaging data set can include counts (also sometimes called samples or events) of oppositely directed 511 keV gamma rays traveling along lines of response (LORs). Each LOR is defined as the line connecting the two radiation detector pixels that detect the two respective 511 keV gamma rays of the oppositely directed pair. At least the counts along LORs both connected by TOF detector pixels 14 have TOF localization information. In other words, the LORs having TOF localization are obtained by the higher speed radiation detector pixels 14. Counts along LORs that have non-TOF localization (i.e., no TOF localization or coarser TOF localization than the TOF localization of the LORs detected by the higher speed radiation detector pixels 14) are obtained by at least one of the lower speed radiation detector pixels 16. The LORs can be identified as being defined by two timestamped 511 keV detection events. Thus, the data at operation 104 include a mix of TOF counts and non-TOF counts having no TOF information. In variant embodiments, the data at operation 104 include a mix of TOF counts and counts with TOF information at coarser resolution.

At 104, fine resolution information is generated from the imaging data generated by the higher speed radiation detector pixels 14. To do so, two coincident timestamped 511 keV detection events (or event pairs) both detected by the higher speed radiation detector pixels 14 via the TOF timestamp circuitry 24 are processed based on the time difference between the two 511 keV detection events to generate TOF localization information. In this operation, the TOF localization information generated for the LORs has finest resolution when both 511 keV detection events are detected by the higher speed radiation detector pixels 14.

At 106, coarse resolution information is generated from the imaging data generated by at least one of the lower speed radiation detector pixels 16. In one example, two coincident timestamped 511 keV detection events (or event pairs) are detected by two of the lower speed radiation detector pixels 16 via the non-TOF timestamp circuitry 30. In this example, the timestamps provided by the timestamp circuitry 30 is sufficient to identify coincident 511 keV detection events (i.e. both timestamps lie within a designated coincidence window), but are of too coarse resolution to provide a finite time difference with sufficient accuracy to derive TOF localization information. In this case it is only known that the annihilation event occurred somewhere along the LOR. In a variant embodiment, the timestamp circuitry 30 does provide sufficient resolution for TOF localization, but at coarser resolution than that provided by the TOF pixels 14 and associated circuitry 24.

In another possibility, two coincident timestamped 511 keV detection events (or event pairs) may be detected, one by one of the lower speed radiation detector pixels 16 and the other by one of the higher speed TOF radiation detector pixels 14. TOF localization may be generated for these types of counts if the lower speed detector pixels 16 provide sufficient temporal resolution, but the resulting TOF localization will again be coarser than that of the data generated on operation 104. In embodiments in which the lower speed detector pixels 16 and/or circuitry 30 are too slow to provide TOF localization, then any events along LORs detected using one pixel 14 and the other pixel 16 will have no associated TOF information.

In some embodiments, there may be no counts along LORs connecting TOF detector pixels 14 and non-TOF detector pixels 16. For example, in the embodiments of FIGS. 2 and 3 each detector ring contains exclusively TOF detector pixels 14, or exclusively non-TOF detector pixels 16. If the acquisition processing performs coincidence processing on a per-ring basis and does not consider counts in which the two 511 keV gamma rays are detected by different detector rings, then the case of LORs connecting TOF detector pixels 14 and non-TOF detector pixels 16 will never occur. By way of non-limiting illustration, such acquisition processing is sometimes employed to generate a two-dimensional (2D) sinogram acquired by each detector ring, which is then reconstructed into a corresponding 2D image slice for that detector ring using a Radon transform or the like. A 3D image can then be constructed as the stack of 2D image slices acquired by the rings of the detector array 10.

At 108, the PET imaging data is reconstructed from both the fine resolution information and the coarse resolution information. The fine resolution information can include the TOF LORs (i.e., generated from the higher speed radiation detector pixels 14) and the coarse resolution information can include the coarse LORs (i.e., generated from the lower speed radiation detector pixels 16). The coarse resolution can also include intermediate LORs (i.e., generated from one of the lower speed radiation detector pixels 16 and one of the higher speed radiation detector pixels 14).

In one example, the reconstructing operation 108 can be performed iteratively. To do so, at first TOF LOR are reconstructed to form an initial TOF reconstructed image. The initial TOF reconstructed image is then input into a first one of the non-TOF LORs to form an initial non-TOF reconstructed image. The initial non-TOF reconstructed image is then input into a second TOF LOR to form a second TOF reconstructed image. The second TOF reconstructed image is then input into a second non-TOF LOR to form a second non-TOF reconstructed image. This iterative process is repeated until all of the TOF LORs have been reconstructed to generate a first reconstructed image, and all of the non-TOF LORs have been reconstructed to generate a second reconstructed image.

In another example, the reconstructing operation 108 is performed using an iterative reconstruction process that operates simultaneously on the fine resolution data from operation 104 and the coarse resolution information from operation 106. To do so, the TOF count j localization information (generated at 104) can include a TOF localization width $\sigma_j = \sigma_F \sqrt{2}$, where $\sigma_F$ is the time resolution of full width at half maximum (FWHM) of the higher speed radiation detector pixels 14. In addition, the lower TOF resolution LOR localization information (generated at 106) can include a TOF localization width $\sigma_j = \sigma_S \sqrt{2}$, where $\sigma_S$ is the time resolution of FWHM of $\sigma_S$ where $\sigma_S > \sigma_F$ (and $\sigma_S$ may be equal to very large values (2-3 ns) of the lower speed radiation detector pixels 16. This implies that $\sigma_S > \sigma_F$. If the coarse resolution counts from operation 106 have no TOF localization at all, this can be modeled by setting $\sigma_S$ to a large value (e.g. 2-3 ns) so that the TOF "localization" is comparable with the entire length of the LOR between the two detectors and possesses negligible information about the true annihilation origin. If both detector pixel types 14, 16 provide TOF localization, then a detection using both detector elements types suitably creates a count with intermediate localization width $\sigma_j = \sqrt{(\sigma_F)^2 + (\sigma_S)^2}$ for the intermediate LOR type. An illustrative iterative reconstruction formulation can be expressed as:

$$f_i^{(n+1)} = \frac{f_i^{(n)}}{S_i} \sum_{g_j} \frac{H_{ij}(\sigma_j) \cdot g_j}{\sum_i H_{ij}(\sigma_j) f_i^{(n)} + \mathrm{Corr}_j(\sigma_j)}$$

where the index i indexes image voxels of the reconstructed image, the index j indexes the LORs, each $g_j$ denotes a count(s) along the LOR j, and the superscripts (n) and (n+1) denote the last and current iterations of the iterative reconstruction, respectively. $H_{ji}(\sigma_j)$ and $H_{ij}(\sigma_j)$ are the forward and backward projection operators (system matrix, depends on the time-of-flight resolution $\sigma_j$ and may include point spread function modeling). The summation is performed over all counts $g_j(\sigma_j)$ for LORs that intersect the image voxel indexed by i. $\mathrm{Corr}_j$ are various optional corrections (e.g. scatter and/or randoms) factors, that may also be dependent on the $\sigma_j$. The factor $S_i$ is the matrix element of the sensitivity matrix corresponding to image voxel i. This update is applied for all image voxels of the image volume to update the image from iteration (n) to iteration (n+1). In the update equation, the localization detector's elements timing resolutions $\sigma_F$, $\sigma_S$, and resulting $\sigma_j$ are employed in the projection operators $H_{ji}$ and $H_{ij}$ and/or the count information $g_j$ depending upon the iterative TOF image reconstruction formulation. It is to be understood that the foregoing update equation is an illustrative general form, and that the iterative image reconstruction may implement various specific iterative image reconstruction algorithms, e.g. maximum likelihood-expectation maximization (MLEM)

image reconstruction, ordered subset expectation maximization (OSEM), or so forth, with appropriate insertion of the timing resolution $\sigma_j$ to capture the TOF localization resolution of the different count types.

EXAMPLES

In detail, when a system is designed with a mixture of TOF and non-TOF detector pixels as disclosed herein, the detector arrangement is preferably chosen based on the goals to achieve. In one example, it is desirable to have a PET system that allows for the acquisition of a complete dataset of high resolution 320 ps-TOF data so that a complete high-resolution TOF image can be reconstructed. In another example, it is desirable to have a PET system that has a total sensitivity twice that from the TOF detectors only (i.e., the system acquires the same amount of non-TOF (or low-resolution TOF) counts as TOF counts). In a further example, it is desirable to have a PET system that can achieve a ~600 ps-TOF image with double the counts from the TOF detectors.

Figure 5:
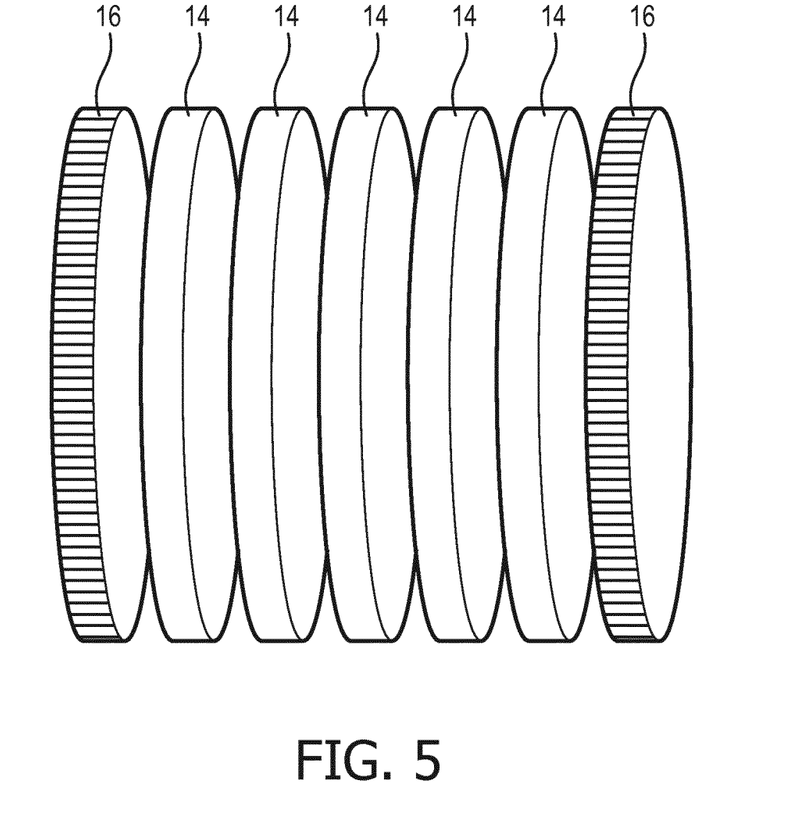
FIG. 5 diagrammatically illustrates an example of the PET detector array of the PET imaging device of FIG. 1

To accomplish these objectives, one example of a PET imaging device is shown in FIG. 5. As shown in FIG. 5, a layout of the form of FIG. 2 is employed, with five 320 ps-TOF rings 14 are disposed in the center of a detection ring (not shown) and one non-TOF ring 16 to each side of the five TOF rings form an effective seven ring PET system. The detector array can acquire a 320 ps-TOF dataset with N counts and a non-TOF dataset with also N counts (approximately). A 320 ps-TOF image will be reconstructed from the N TOF counts. The joint TOF and non-TOF reconstruction using both the N TOF counts and the N non-TOF counts will reconstruct an image similar to that of a dataset with 2N 600 ps-TOF counts.

More explicitly, FIG. 5 illustrates a design that extends the axial field-of-view (aFOV) of a five-ring TOF system from 16.4 cm to 23.0 cm by adding two edge non-TOF rings. Total sensitivity of the system is doubled, but the cost of the two non-TOF rings can be much lower than adding two TOF rings. For example, the sensitivity from the TOF detector rings is about 5,400 cnts/MBq. With the added two non-TOF rings, the total sensitivity is doubled to be about 10,800 cnts/MBq. With the optimized joint reconstruction of the TOF and non-TOF data, an image quality can be achieved that is similar to a system with 10,800 cnts/MBq sensitivity with TOF resolution of 600 ps. Using the same overlapping scheme as is used in Vereos, a full data set of the patient with 320 ps TOF, can be acquired and a 320 ps-TOF image of the patient from the aFOV-TOF data can be reconstructed. In the meanwhile, a ~600 ps-TOF image of the patient from the aFOV-Total data can be reconstructed, which has twice the number of counts as the 320 ps-TOF data.

The image acquisition protocol or clinical workflow can be developed based on the requirement and the system configuration/design as described above. For the example shown in FIG. 5, an acquisition protocol using table/bed overlaps similar to a five ring TOF system will allow the acquisition of a complete set of TOF data, so a complete TOF reconstruction of the patient can be obtained. The non-TOF or low-TOF data of the same patient, can be used to reconstruct a higher count density image using the joint TOF and non-TOF (or low-resolution TOF) reconstruction.

The example PET system shown in FIG. 5 allows for a joint reconstruction of TOF and non-TOF (or low-resolution TOF) data. When reconstructed independently, the non-TOF data only leads to a non-TOF image that have been shown to be inferior to TOF images in lesion detection, data inconsistency handling, etc. The joint reconstruction, however, can use the TOF data to guide the reconstruction of the non-TOF data, so that the latter effectively "inherits" some TOF information from the TOF data. Or in other words, the TOF data passes some TOF information to the non-TOF data reconstruction. It is desirable to optimize the use of the TOF data to guide the reconstruction of the non-TOF data.

One approach to the joint reconstruction is to reconstruct the TOF image and non-TOF image in an interleaved manner in iterative reconstruction (the iterative reconstruction can be either list-mode or non-list-mode). One first performs a TOF reconstruction with one TOF update to get the first TOF image, then pass the TOF image to non-TOF reconstruction, using the TOF image as the initial image in the forward projection step for non-TOF update; Once the non-TOF update is finished, it is passed to the TOF reconstruction as the initial image for the second TOF update, and so on. With this approach, the joint reconstruction of 320 ps-TOF data and non-TOF data obtained image slightly better than 600 ps-TOF image for data inconsistency handling (FIGS. 6 and 7) in noise-free simulation and lesion detection and noise control (FIG. 8) in noisy simulation.

Figure 6:
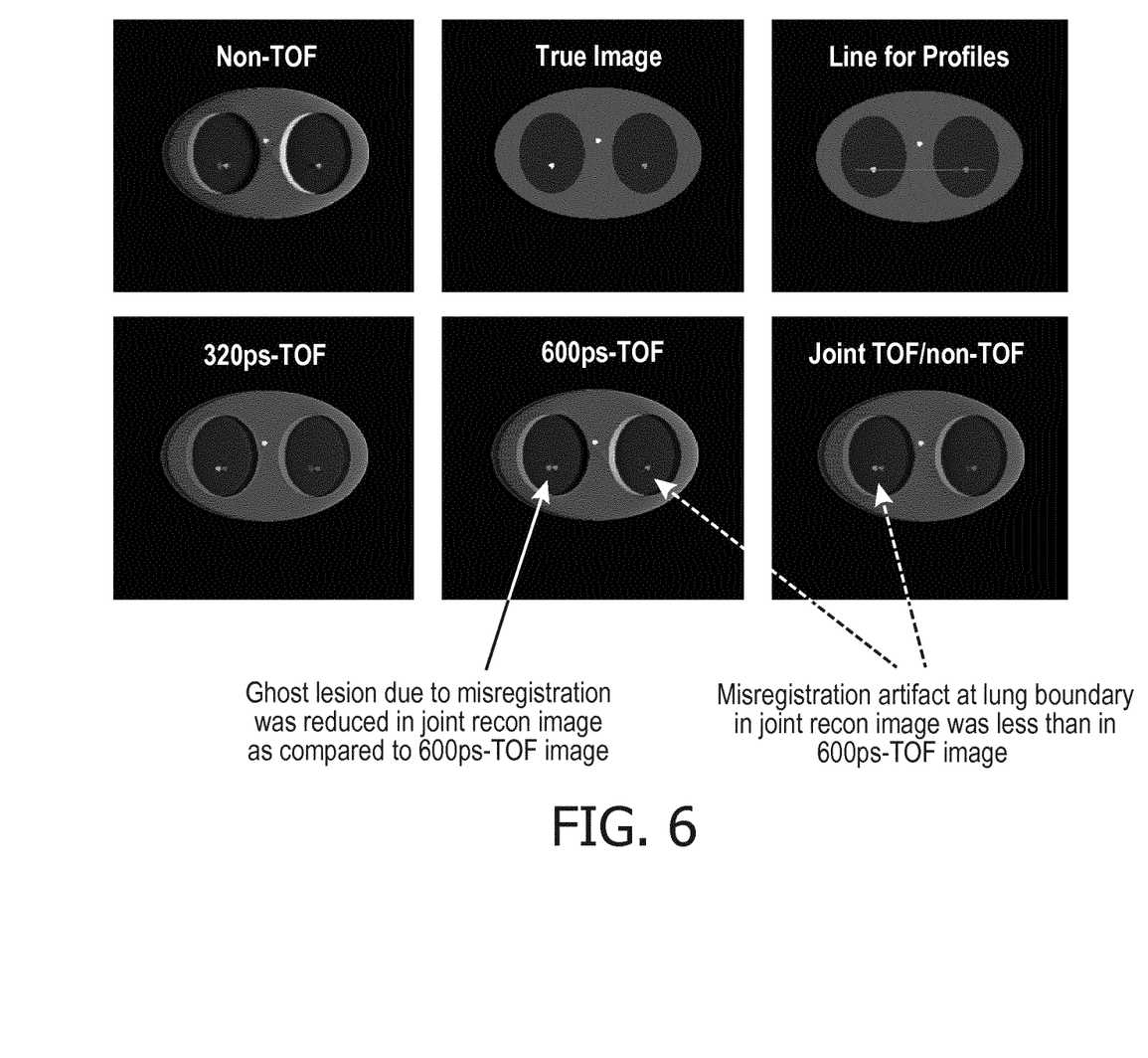
FIGS. 6-8 show graphs representing operations of the PET detector array of FIG. 5.
Figure 7:
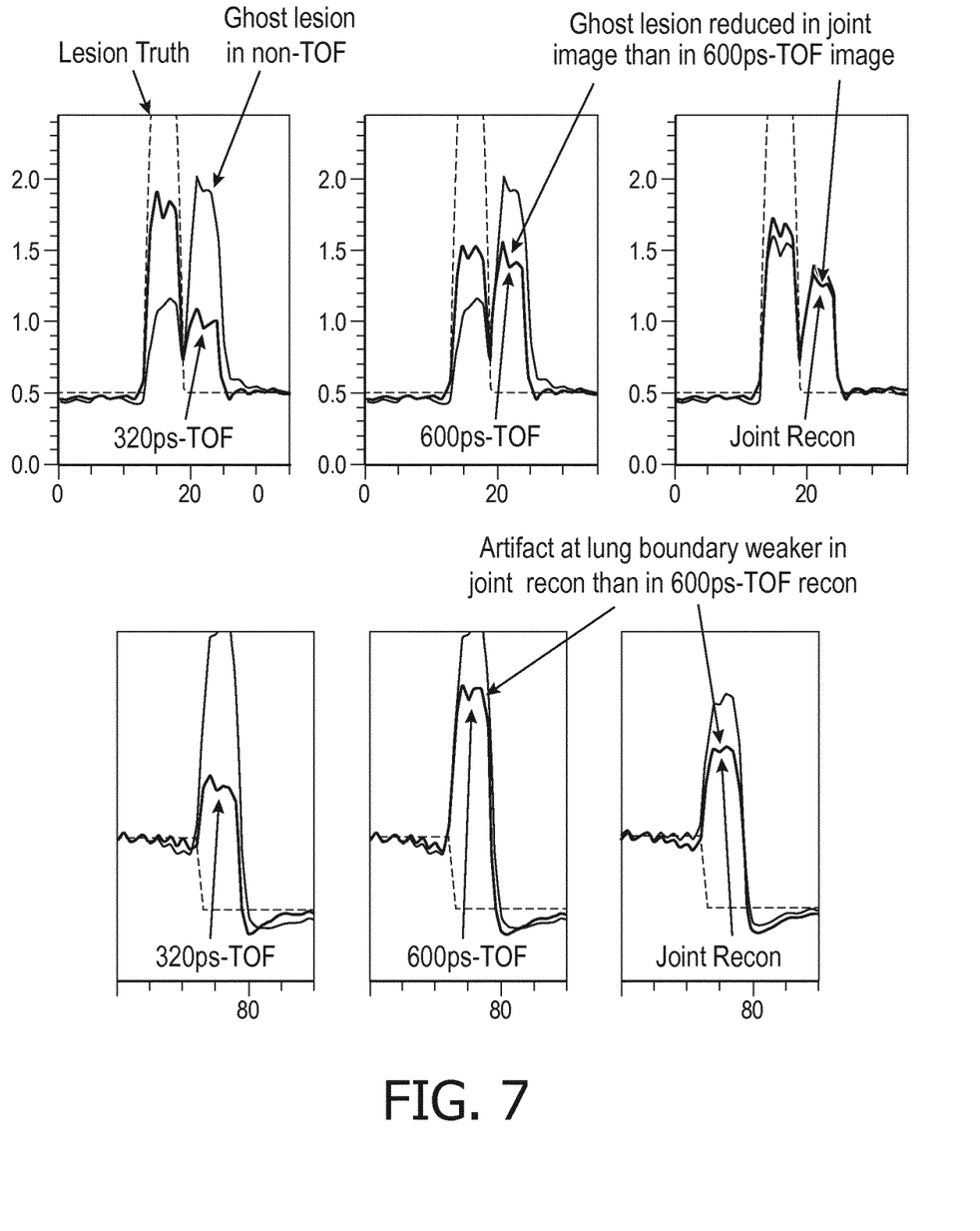

FIGS. 6 and 7 show graphs representing joint TOF (320 ps resolution) and non-TOF reconstruction showed better handling of PET/CT misregistration than 600 ps-resolution TOF, e.g., reduced artifacts, improved true lesions. In this simulation the CT image for attenuation correction was shifted to the left of the PET image by 12 mm. FIG. 6 shows reconstructed images, while FIG. 7 shows line profile comparison.

Figure 8:
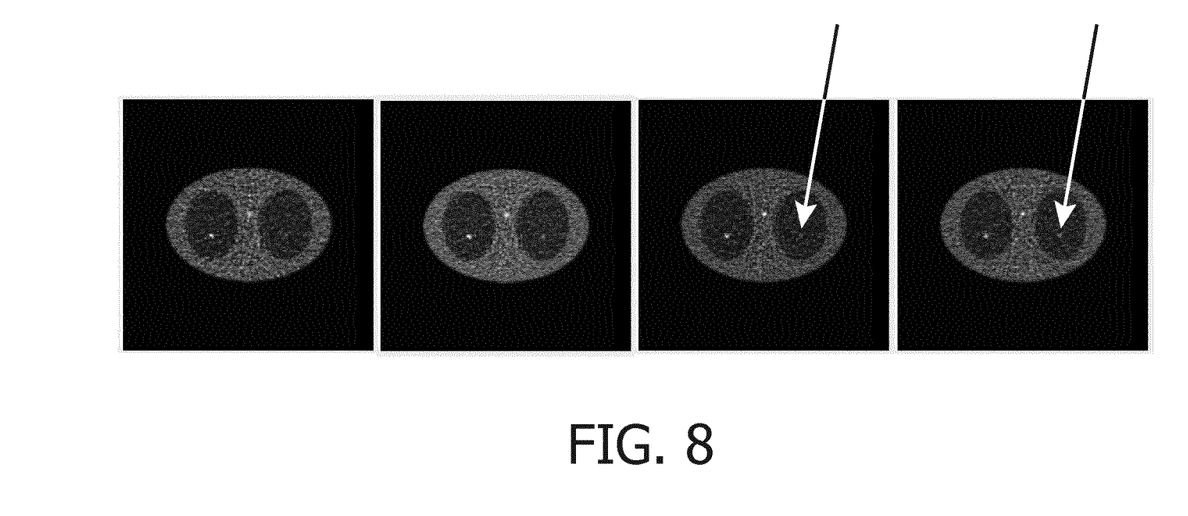

FIG. 8 shows graphs representing simulation studies showing joint reconstruction of 320 ps-TOF data and non-TOF data obtained same or better lesion detection and noise suppression than 600 ps-TOF data. The right lung lesion detection was comparable for the joint recon and the 600 ps-TOF recon, but the left lung lesion was better in the joint recon than the 600 ps-TOF image (highlighted by arrows). As shown in FIG. 8, the 320 ps-TOF image was the best, and the non-TOF image was the poorest.

More advanced optimization of joint TOF/non-TOF reconstruction is expected to further improve the image quality reconstructed from both the TOF and non-TOF data. For example, one can use the TOF image as a prior for non-TOF image reconstruction not only as the initial image for the forward projection process as described above, but also use it in the back projection process of the iterative reconstruction also. Another example is to use the scatter estimation from the TOF data in non-TOF data reconstruction to improve the accuracy of scatter correction for the non-TOF data.

It will be appreciated that the illustrative computational, data processing or data interfacing components of the PET imaging device 1 may be embodied as a non-transitory storage medium storing instructions executable by an electronic processor (e.g., the processor 44) to perform the disclosed operations. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth.

The disclosure has been described with reference to the preferred embodiments. Modifications and alterations may occur to others upon reading and understanding the preceding detailed description. It is intended that the disclosure be constructed as including all such modifications and altera-

The invention claimed is:

1. A positron emission tomography (PET) detector array, comprising:
an enclosing radiation detector array comprising radiation detector elements effective for detecting 511 keV radiation emanating from inside the enclosing radiation detector array;
wherein the radiation detector elements of the enclosing radiation detector array include both time-of-flight (TOF) detector elements with TOF timestamp circuitry generating time stamps for 511 keV radiation detection events detected by the TOF radiation detector pixels with temporal resolution effective to provide TOF localization along lines of response (LORs), and non-TOF radiation detector elements with non-TOF timestamp circuitry generating time stamps for 511 keV radiation detection events detected by the lower speed radiation detector pixels with temporal resolution that is too coarse to provide TOF localization along LORs.

2. The PET detector array of claim 1, wherein the enclosing radiation detector array is a cylindrical radiation detector array that comprises a plurality of radiation detector rings arranged to form the cylindrical radiation detector array.

3. The PET detector array according to claim 2, wherein the radiation detector elements comprises pixels, and the plurality of radiation detector rings includes:
central radiation detector rings forming a central portion of the cylindrical detector array wherein each central radiation detector ring includes the TOF radiation detector pixels and does not include any of the non-TOF radiation detector pixels; and
peripheral radiation detector rings forming peripheral portions of the cylindrical detector array wherein each peripheral radiation detector ring includes the non-TOF radiation detector pixels and does not include any of the TOF radiation detector pixels.

4. The PET detector array of claim 1, wherein the radiation detector array comprises a plurality of detector modules and each detector module includes only the TOF radiation detector pixels or only the non-TOF radiation detector pixels.

5. The PET detector array according to claim 1, w % herein the TOF radiation detector pixels comprise one of Lutetium-yttrium oxyorthosilicate (LYSO) Lutetium oxyorthosilicate (LSO), Lutetium Fine Silicate (LFS) or Lanthanum Bromide (LaBr) scintillators, and the non-TOF radiation detector pixels comprise Bismuth Germanate Oxide (BGO) or Sodium Iodide (NaI) scintillators.

6. The PET detector array of claim 1, further comprising:
an electronic processor; and
a non-transitory storage medium storing instructions readable and executable by the electronic processor to perform operations including:
identifying counts comprising lines of response (LORs) wherein each count is defined by two timestamped 511 keV detection events; and
generating TOF localization information for each count defined by two timestamped 511 keV detection events both detected by the TOF radiation detector pixels.

7. The PET detector array of claim 6, wherein said operations further include:
also generating TOF localization information for each LOR defined by two timestamped 511 keV detection events at least one detected by one of the non-TOF radiation detector pixels;
wherein the TOF localization information generated for the counts has finest timing resolution when both 511 keV detection events are detected by the TOF radiation detector pixels, has coarsest or non-existent timing resolution when both 511 keV detection events are detected by the non-TOF radiation detector pixels, and has intermediate resolution when one of the 511 keV detection events is detected by one of the TOF radiation detector pixels and the other of the 511 keV detection events is detected by one of the non-TOF radiation detector pixels.

8. A positron emission tomography (PET) imaging device, comprising:
a radiation detector array comprising both time-of-flight (TOF) radiation detector pixels and lower speed radiation detector pixels wherein the lower speed radiation detector pixels have a temporal resolution that is coarser than a temporal resolution of the TOF radiation detector pixels, wherein the radiation detector array comprises a plurality of detector modules and each detector module includes only the higher speed radiation detector pixels or only the lower speed radiation detector pixels;
an electronic processor; and
a non-transitory storage medium storing instructions readable and executable by the electronic processor to perform operations including:
generating fine TOF counts along lines of response (LORs) with TOF localization from coincident 511 keV detection event pairs both detected by TOF radiation detector pixels of the radiation detector array;
generating coarse TOF resolution counts from coincident 511 keV detection event pairs in which at least one event of the pair is detected by a lower speed radiation detector pixel of the radiation detector array, the coarse LORs being generated with no TOF localization or with TOF localization that is coarser than the TOF localization of the TOF LORs; and
reconstructing a PET data set comprising both the fine TOF LORs and the coarse TOF LORs to generate a reconstructed image.

9. The PET imaging device of claim 8, wherein the radiation detector array comprises a plurality of radiation detector rings arranged to form the radiation detector array.

10. The PET imaging device according to claim 9, wherein the plurality of radiation detector rings includes:
central radiation detector rings forming a central portion of the cylindrical detector array wherein each central radiation detector ring includes the higher speed radiation detector pixels and does not include any of the lower speed radiation detector pixels; and
peripheral radiation detector rings forming peripheral portions of the cylindrical detector array wherein each peripheral radiation detector ring includes the lower speed radiation detector pixels and does not include any of the higher speed radiation detector pixels.

11. The PET imaging device of claim 10, wherein:
each central radiation detector ring includes time-of-flight (TOF) timestamp circuitry generating time stamps for 511 keV radiation detection events detected by the higher speed radiation detector pixels with temporal resolution effective to provide TOF localization along lines of response (LORs); and each peripheral radiation detector ring includes non-TOF timestamp circuitry generating time stamps for 511 keV radiation detection events detected by the lower speed radiation detector pixels with temporal resolution that is too coarse to provide TOF localization along LORs.

12. The PET imaging device according to claim 8, wherein the higher speed radiation detector pixels comprise one of Lutetium-yttrium oxyorthosilicate (LYSO) Lutetium oxyorthosilicate (LSO), Lutetium Fine Silicate (LFS) or Lanthanum Bromide (LaBr) scintillators, and the lower speed radiation detector pixels comprise Bismuth Germanate Oxide (BGO) or Sodium Iodide (NaI) scintillators.

13. The PET imaging device of claim 12, wherein the reconstructing includes iteratively:

reconstructing the fine TOF counts to generate a first reconstructed image; and reconstructing the coarse TOF counts to generate a second reconstructed image;

wherein the reconstructing the TOF LORs uses the second image and the reconstructing of the coarse LORs uses the first reconstructed image.

14. The PET imaging device of claim 12, wherein the time-of-flight (TOF) radiation detector pixels possess timing resolution of full width at half maximum (FWHM) $\sigma_F$, the coarser, lower speed radiation detector pixels possess timing resolution of FWHM of $\sigma_S$ where $\sigma_S > \sigma_F$, and the reconstructing comprises iterative reconstruction employing projection operators $H_{ij}(\sigma_j)$ where j indexes a LOR, i indexes an image voxel, and $\sigma_j = \sigma_F \sqrt{2}$ for the TOF LORs and $\sigma_j = \sigma_S \sqrt{2}$ for the coarse LORs.

15. A non-transitory storage medium storing instructions readable and executable by at least one processor to perform a positron emission tomography (PET) image reconstruction method, the method including:

receiving or generating a PET data set comprising counts along lines of response (LORs) wherein the PET data set includes at least first count type with time-of-flight (TOF) localization and second count type with no TOF localization; and reconstructing the entire PET data set including both the first count type and the second count type to generate a reconstructed image.

16. The non-transitory storage medium of claim 15, wherein the reconstructing includes iteratively:

reconstructing the first count type to generate a first reconstructed image; and reconstructing the second count type to generate a second reconstructed image;

wherein the reconstructing the first count type uses the second image and the reconstructing of the second count type uses the first reconstructed image.

17. The non-transitory storage medium of claim 15, wherein the PET data set is generated using TOF-capable detector elements and non-TOF capable detector elements, the TOF-capable detector elements have timing resolution of $\sigma_F$, the non-TOF detector elements have timing resolution of $\sigma_S$ where $\sigma_S > \sigma_F$, and the reconstructing comprises iterative reconstruction employing projection operators $H_{ij}(\sigma_j)$ where j indexes a count or projection bin, i indexes an image voxel, and $\sigma_j = \sigma_F \sqrt{2}$ for the LORs of the first count type and $\sigma_j = \sigma_S \sqrt{2}$ for LORs of the second count type.

18. The non-transitory storage medium of claim 15, wherein:

the first count type include TOF localization of width $\sigma_j = \sigma_F \sqrt{2}$ and the second count type include TOF localization of width $\sigma_j = \sigma_S \sqrt{2}$ where $\sigma_S > \sigma_F$;

the PET data set further comprises third counts type with TOF localization of width $\sigma_j$ wherein TOF resolution is estimated as $\sigma_j = \sqrt{(\sigma_F)^2 + (\sigma_S)^2}$; and the reconstructing comprises reconstructing the entire PET data set including the first count type and the second count type and the third count type to generate the reconstructed image.

* * * * *